United States Patent [19]
Dufetel et al.

[11] Patent Number: 5,438,058
[45] Date of Patent: Aug. 1, 1995

[54] COMPOSITION INTENDED TO BE USED FOR RETARDING HAIR LOSS AND FOR INDUCING AND STIMULATING HAIR GROWTH, CONTAINING 2-ALKYL-4-AMINOPYRIMIDINE (OR 2,4-DIALKYLPYRIMIDINE) 3-OXIDE DERIVATIVES AND NEW COMPOUNDS DERIVED FROM 2-ALKYL-4-AMINOPYRIMIDINE 3-OXIDE

[75] Inventors: Didier Dufetel, Chelles; Françoise Estradier; Michel Hocquaux, both of Paris, all of France

[73] Assignee: L'Oreal, Paris, France

[21] Appl. No.: 221,443

[22] Filed: Apr. 1, 1994

Related U.S. Application Data

[63] Continuation of Ser. No. 707,747, May 30, 1991, abandoned.

[30] Foreign Application Priority Data

May 30, 1990 [FR] France .................. 90 06693

[51] Int. Cl.$^6$ .................. A61K 31/505; C07D 239/24
[52] U.S. Cl. .................. 514/252; 514/256; 544/226; 544/295; 544/319; 544/328; 544/329
[58] Field of Search .............. 544/226, 295, 319, 328, 544/329; 514/255, 256, 252

[56] References Cited

U.S. PATENT DOCUMENTS

| | | | |
|---|---|---|---|
| 3,551,420 | 12/1970 | Anthony | 544/123 |
| 4,139,619 | 2/1979 | Chidsey, III | 424/45 |
| 4,885,296 | 12/1989 | Manoury et al. | 514/252 |
| 4,945,093 | 7/1990 | Maignan et al. | 514/235.8 |
| 4,973,474 | 11/1990 | Hocquaux et al. | 424/70 |

FOREIGN PATENT DOCUMENTS

| | | |
|---|---|---|
| 0015364 | 9/1980 | European Pat. Off. |
| 0303871 | 2/1989 | European Pat. Off. |
| 0356271 | 2/1990 | European Pat. Off. |
| 0384370 | 8/1990 | European Pat. Off. |
| 1143167 | 2/1969 | United Kingdom |
| WO8504577 | 10/1985 | WIPO |
| WO8604231 | 7/1986 | WIPO |

OTHER PUBLICATIONS

Chemical Abstracts 100:191818 (1984).
Chemical Abstracts 84:121,760 (1976).
Chemical Abstracts 101:55,034 (1984).
Chemical Abstracts: 113:197,661 (1990).

*Primary Examiner*—Mukund J. Shah
*Assistant Examiner*—Matthew V. Grumbling
*Attorney, Agent, or Firm*—Jacobson, Price, Holman & Stern

[57] ABSTRACT

Pharmaceutical or cosmetic composition intended to be used, by topical application, for retarding hair loss and for inducing or stimulating hair growth, containing at least one compound of formula:

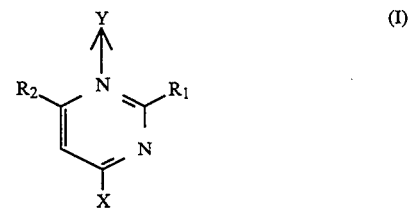

where:
$R_1$ denotes H or $C_1$-$C_8$ alkyl;
$R_2$ denotes $C_1$-$C_8$ alkyl or $NHR_3$, where $R_3$ denotes H or —$COOR_4$, where $R_4$ denotes $C_1$-$C_4$ alkyl;
X denotes

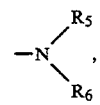

—$OR_9$ or —$SR_{10}$;
$R_5$ and $R_6$ denote H, optionally substituted $C_1$-$C_{12}$ alkyl, or $C_2$-$C_{12}$ alkenyl, $C_3$-$C_{10}$ cycloalkyl, aralkyl or aryl, or form, with N, a saturated or unsaturated heterocycle;
$R_9$ denotes optionally substituted $C_1$-$C_{12}$ alkyl, or $C_2$-$C_{12}$ alkenyl, $C_3$-$C_{10}$ cycloalkyl, $C_7$-$C_{12}$ aralkyl or phenyl, which may optionally be substituted;
$R_{10}$ is identical to $R_9$; and
Y denotes O or $OSO_3^\ominus$;

as well as its cosmetically or pharmaceutically acceptable acid addition salts.

17 Claims, No Drawings

COMPOSITION INTENDED TO BE USED FOR RETARDING HAIR LOSS AND FOR INDUCING AND STIMULATING HAIR GROWTH, CONTAINING 2-ALKYL-4-AMINOPYRIMIDINE (OR 2,4-DIALKYLPYRIMIDINE) 3-OXIDE DERIVATIVES AND NEW COMPOUNDS DERIVED FROM 2-ALKYL-4-AMINOPYRIMIDINE 3-OXIDE

This application is a continuation of application Ser. No. 07/707,747, filed May 30, 1991, now abandoned.

The invention relates to compositions intended to be used, in particular by topical application, for retarding hair loss and for inducing and stimulating hair growth, containing 2-alkyl-4-aminopyrimidine (or 2,4-dialkylpyrimidine) 3-oxide derivatives, as well as new 2-alkyl-4-aminopyrimidine 3-oxide derivatives used in these compositions.

2,4-Diamino-6-piperidinopyrimidine 3-oxide or "Minoxidil" is already known in the prior art for its properties as an anti-hypertensive agent, but also for its use in the treatment of hair loss, pelade, desquamative dermatitis and alopecia.

The Applicant has discovered new compositions for the treatment and the prevention of hair loss, which compositions are used in particular by topical application and contain a particular family of compounds derived from 2-alkyl-4-aminopyrimidine 3-oxide or 2,4-dialkylpyrimidine 3-oxide.

The compounds considered by the Applicant are effective for the regrowth of hair and in particular for inducing and stimulating hair growth and retarding hair loss and, in contrast to Minoxidil, have a hypertensive activity which is substantially zero or weaker.

Moreover, these compounds have solubilities in the media customarily used in cosmetics and in pharmacy which are clearly higher than those of Minoxidil.

The invention therefore relates to new compositions intended for the treatment and the prevention of hair loss, containing particular compounds derived from 2-alkyl-4-aminopyrimidine (or 2,4-dialkylpyrimidine) 3-oxide.

The invention also relates to new 2-alkyl-4-aminopyrimidine 3-oxide derivatives used in these compositions.

A further subject relates to the use of the compounds according to the invention for the preparation of a medicament intended for the therapeutic treatment of hair loss.

Other subjects of the invention will become apparent on reading the description and the examples which follow.

The compositions according to the invention are essentially characterised in that they contain, in a physiologically acceptable medium, at least one compound corresponding to the following formula:

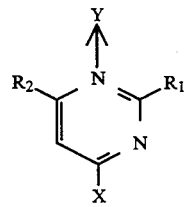

(I)

in which:

$R_1$ denotes a hydrogen atom or a $C_1$-$C_8$ saturated straight-chain alkyl radical;

$R_2$ denotes a $C_1$-$C_8$ saturated straight-chain alkyl radical, an —$NHR_3$ group in which $R_3$ denotes a hydrogen atom, or the group —$COOR_4$, where $R_4$ represents a $C_1$-$C_4$ straight-chain alkyl radical;

X denotes:

(i) a

group
in which:

$R_5$ and $R_6$, which may be identical or different, denote a hydrogen atom, a straight-chain or branched $C_1$-$C_{12}$ alkyl group, which may be substituted by one or more halogen atoms, a $C_2$-$C_{12}$ straight-chain alkenyl group, a $C_3$-$C_{10}$ cycloalkyl group or an aryl or aralkyl group corresponding to the formula:

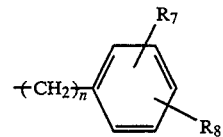

where n ranges from 0 to 4; and $R_7$ and/or $R_8$, independently of one another, denote a hydrogen atom, a $C_1$-$C_6$ lower alkyl or alkoxy group or a trifluoromethyl radical; and $R_5$ and $R_6$, together with the nitrogen atom to which they are bonded, may form a saturated or unsaturated heterocycle chosen from the following groups: aziridinyl, azetidinyl, pyrrolidinyl, piperidinyl, hexamethyleneimino, heptamethyleneimino, octamethyleneimino, tetrahydropyridyl, dihydropyridyl, pyrrolyl, pyrazolyl, imidazolyl, triazolyl, 4-alkylpiperazinyl, morpholino and thiomorpholino;

(ii) an —$OR_9$ group, in which $R_9$ denotes a straight-chain or branched $C_1$-$C_{12}$ alkyl radical, which may be substituted by one or more halogen atoms, a $C_2$-$C_{12}$ alkenyl radical, a $C_3$-$C_{12}$ cycloalkyl radical, a $C_7$-$C_{12}$ aralkyl radical or a phenyl radical, which may optionally be substituted by one or two groups which, independently of one another, denote a $C_1$-$C_6$ alkyl radical, a $C_1$-$C_6$ alkoxy radical, a halogen atom or a trifluoromethyl radical; or (iii) an —$SR_{10}$ group, in which $R_{10}$ has the same meaning as the radical $R_9$ defined above; and Y denotes an oxygen atom or an —$OSO_3^{\ominus}$ group.

Amongst the compounds of general formula ( I ), according to the present invention, in which X denotes a

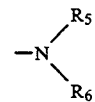

group, the compounds which are particularly preferred are those for which:

$R_2$ denotes a methyl radical and X denotes the piperidino group; or $R_2$ denotes an —$NHR_3$ group, in which $R_3$ has the meaning mentioned in the definition of formula (I) and X denotes one of the following amino groups: dimethylamino, diethylamino, n-butylamino, piperidino, morpholino, 4-methylpiperazinyl, benzylamino or anilino.

Amongst the compounds of general formula (I), according to the present invention, in which X denotes the —$OR_9$ group, the compounds which are particularly preferred are chosen from those for which:

$R_2$ denotes a methyl radical and X denotes the ethoxy group; or $R_2$ denotes the —$NHR_3$ group, in which $R_3$ has the meaning indicated in formula (I) and X denotes the following alkoxy groups: ethoxy, butoxy, 1-methylethoxy and 2,4-dimethylphenoxy.

When Y denotes an oxygen atom and $R_2$ denotes the —$NHR_3$ group, the compounds of formula (I) exist in two tautomeric forms, in accordance with the equilibrium below:

[Structures (I) and (I$_2$) showing tautomeric equilibrium]

Depending on the nature of the medium, one of the forms may be predominant relative to the other.

The compounds of formula (I), according to the present invention, may be converted into their cosmetically or pharmaceutically acceptable acid addition salts, such as the salts of sulphuric, hydrochloric, hydrobromic, phosphoric, acetic, benzoic, salicylic, glycolic, succinic, nicotinic, tartaric, maleic, pamoic, methanesulphonic, picric and lactic acids, etc.

Amongst the compounds of general formula (I), some compounds are known per se and have been described as anti-hypertensive agents or as synthesis intermediates.

They are, in particular, described in the U.S. Pat. Nos. 3,464,987 and 4,287,338; or cited in the technical literature (Chem. Pharm. Bull. 29 (1), 98–104 (1981)).

The new compounds, which constitute another subject of the invention, correspond to the following formula (I'):

[Structure (I')]

in which X, Y, $R_2$ and $R_1$ have the same meanings as those indicated in formula (I) above, with the proviso that:

1) When X denotes $$-N\begin{matrix}R_5\\R_6\end{matrix}$$

in which $R_5$ and $R_6$ have the same meaning indicated in formula (I);

if Y denotes O, $R_1$ and $R_2$ denote, independently of one another, a $C_1$-$C_8$ saturated straight-chain alkyl group; and if Y denotes $OSO_3^\ominus$, $R_2$ does not denote $NH_2$; and 2) when X denotes $OR_9$, in which $R_9$ has the same meaning as that indicated above, if Y denotes O, $R_2$ denotes the $NHR_3$ group as defined above.

The new compounds of formula (I') may be in the form of physiologically acceptable acid addition salts.

The compounds according to the present invention which correspond to the general formula (I) are obtained from a pyrimidine 3-oxide derivative substituted in the 6-position, of following formula (II):

[Structure (II)]

in which:

$R_1$ denotes a hydrogen atom or a $C_1$-$C_8$ saturated straight-chain alkyl radical;

$R_2$ denotes an amino group or a $C_1$-$C_8$ saturated straight-chain alkyl radical; and Z denotes a halogen atom chosen from chlorine or bromine, a sulphonate group, such as tosylate, brosylate or mesylate, or a phenoxy group substituted by electron-attracting groups such as halogen atoms or nitro groups.

The compounds of formula (II), depending on the nature of the group Z, may be synthesised in accordance with the following reaction scheme:

[Structures (III) → Step 1 → (IV) → Step 2]

Step 1

The compounds of formula (III) which are hydroxylated in the 6-position are converted to their halogenated or sulphonated derivatives of formula (IV) in which $Z_1$ denotes a halogen atom or a sulphonate group.

The halogenation methods are conventional and described in the technical literature (JERRY MARCH, Advanced Organic Chemistry, 3rd edition, page 593); the halogenating agent most frequently used is a phosphorus oxyhalide, such as phosphorus oxychloride for the chlorination.

The sulphonation methods used are conventional and described in the technical literature (JERRY MARCH, Advanced Organic Chemistry, 3rd edition, page 444). They consist in reacting a sulphonic acid halide, in the presence of a base, with the compounds of formula (III).

Step 2:

The compounds of formula (IV) are easily oxidised in the position para to the $Z_1$ group by the action of an organic peracid, such as metachloroperbenzoic acid, in the presence of a protic or aprotic solvent such as dichloromethane.

Step 3:

The compounds (IV) may be substituted by phenoxy groups $Z_2$ carrying electron-attracting groups, in accordance with the conventional methods described in the literature, in particular French Patent No. 1,513,739 (in particular in the case where $R_2$ denotes $NH_2$).

Step 4:

The compounds (V) resulting from step 3 are oxidised in the position para to the group $Z_2$ by the action of an organic peracid, in accordance with the methods described in French Patent No. 1,513,739.

The particular compounds, according to the invention, corresponding to the formula (IA):

in which $R_1$, $R_2$, $R_5$ and $R_6$ have the meanings indicated in the general formula (I) above, are obtained by reacting an amine with the compounds of formula (II).

The reaction is carried out in the presence of a solvent, which may be an alcohol, preferably ethanol, or of the amine serving as reagent and solvent at the same time, at a temperature of between 20° and 150° C., in accordance with the processes described in U.S. Pat. Nos. 3,644,364 and 3,464,987 where Z denotes a phenoxy group.

The preparation of these compounds may be represented by the following scheme:

SCHEME A

The particular compounds, according to the invention, of formula (IB)

are obtained by reacting a solution of the alcoholate $R_9O^{\ominus}W^{\oplus}$, in which $R_9$ has the same meaning indicated in formula (I) and W denotes an alkali metal, such as sodium, potassium or lithium, in the corresponding alcohol, with the compounds of formula (II), in which Z denotes chlorine or bromine or a phenoxy group substituted by electron-attracting groups.

The Williamson method, as described in European Patent EP-57546, is applied at a temperature of between 40° and 100° C.

The preparation of these compounds may be represented by the following scheme:

SCHEME $B_1$

The compounds of formula (IB) may be obtained by another process represented by the following scheme:

SCHEME B₂

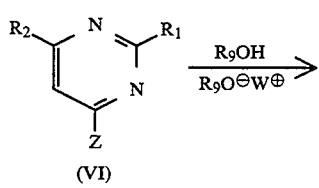

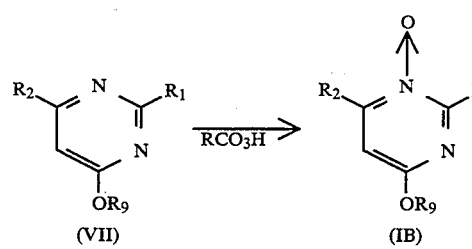

This process consists in carrying out a Williamson reaction on the compound of formula (VI), in which R₂, R₁ and Z have the same meanings indicated in formula (II), in order to obtain a derivative alkoxylated in the 6-position of formula (VII). The latter derivative is then oxidised selectively in the 3-position by a mild organic peracid, such as metachloroperbenzoic acid or magnesium monoperphthalate.

The compounds of formula (IB) are, in general, more accessible by the route of process B₂, in particular for branching of alcoholates sterically hindered in the 6-position, such as the isopropylate.

The particular compounds, according to the invention, corresponding to the formula (IC):

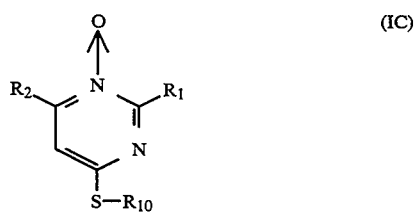

in which R₁, R₂ and R₁₀ have the meanings indicated above, are obtained by reacting a thiolate of formula R₁₀S⊖W⊕, in which R₁₀ and W⊕ have the same meanings as above, with the compounds of formula (II) in the presence of a solvent chosen from ethers, preferably ethylene glycol monomethyl or dimethyl ether, at a temperature of the order of 50° to 150° C.

The reaction is carried out in accordance with the conventional methods from the literature (D. J. Brown, The Pyrimidines, Vol.16, Supplement II, Chapter VI, Section F).

The preparation of these compounds may be represented by the following scheme C:

SCHEME C

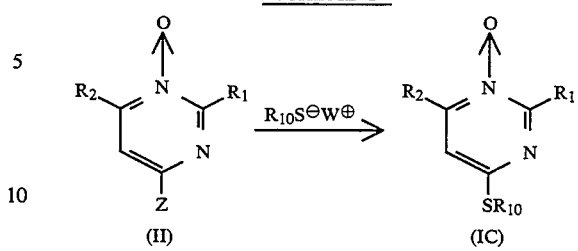

The particular compounds, according to the invention, of formula (I), in which Y denotes an oxygen atom, obtained by the various processes described above, may be converted to their O-sulphate homologues of formula (ID) defined below, by chemical sulphation, in accordance with the conventional methods described in the literature (J. Med. Chem., 1983, 26, p. 1791–1793).

The sulphation reagents used are sulphur trioxide/pyridine, sulphur trioxide/triethylamine or sulphur trioxide/ethyldiisopropylamine complexes.

The solvents used are preferably dimethylformamide, acetonitrile, chloroform or their binary mixtures. The temperature is of the order of 0° to 25° C. and the reaction time varies between 1 hour and 24 hours.

The preparation of the compounds of formula (ID) thus obtained may be represented by the following scheme:

SCHEME D

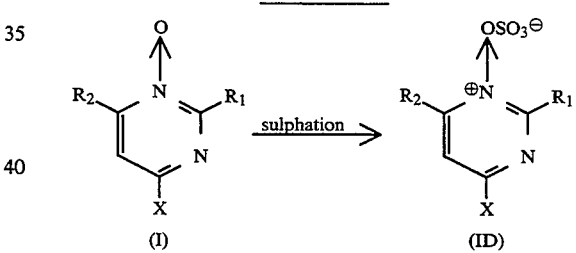

The compounds of general formula (I), according to the invention, in which Y denotes an oxygen atom and R₂ denotes the amino group —NH₂ may be converted to their carbamate homologues of formula (IE) as defined below.

The compounds (IE) are prepared in accordance with the conventional methods from the literature (J. March, Advanced Organic Chemistry, 3rd edition, p.370) by the action of an alkyl chloroformate in the presence of a tertiary amine such as pyridine, as represented by the following scheme:

SCHEME E:

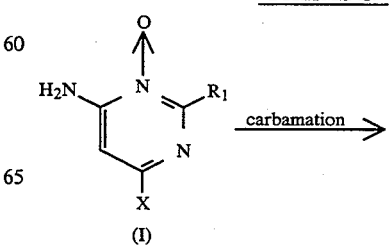

-continued
SCHEME E:

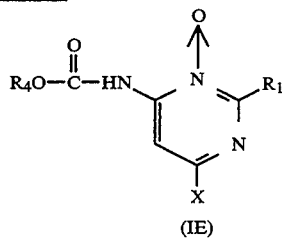

The compounds of formula (IE) are easily hydrolysable in an alcoholic potassium hydroxide medium and may give rise again to their precursors of formula (I) in which Y denotes an oxygen atom and $R_2$ an amino group —$NH_2$.

The compounds of formula (IE), according to the invention, may be intermediates for the synthesis of oxadiazolopyrimidinones having the formula (VIII) defined below:

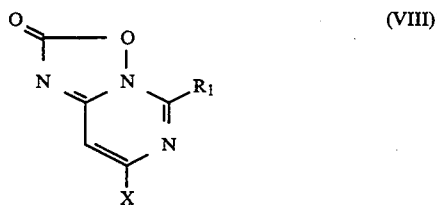

in which $R_1$ and X have the meaning indicated in general formula (I).

The compounds (VIII) are obtained by cyclisation-/internal elimination of the carbamate derivatives of formula (IE), in accordance with the methods described in the literature (J. C. MULLER, Helvetica Chimica Acta, Vol. 66, 1983, p. 669–672).

The compounds of formula (VIII) and their cosmetically and pharmaceutically acceptable acid addition salts are new and constitute another subject of the invention. They may receive various applications and in particular in the use for the treatment and the prevention of hair loss and the stimulation of hair regrowth.

The compositions according to the present invention, containing at least one compound corresponding to the formula (I), or one of its physiologically acceptable acid addition salts, in a physiologically acceptable media may be applied in the cosmetics or pharmaceutical field, in particular by topical application. They are intended for the treatment and the prevention of hair loss, and in particular of pelade or alopecia, as well as desquamative dermatites, and the stimulation of hair regrowth.

These compositions may contain, as physiologically acceptable medium, any medium which is suitable for topical application, either in cosmetics or in pharmacy, and which is compatible with the active substance.

The compounds according to the invention may be present in this medium either in the dissolved state or in the dispersed state, in particular in micronised form.

The compositions intended to be used in pharmacy are in the form of an ointment, dye, cream, pomade, powder, patch, impregnated buffer, vesicular solution, emulsion or dispersion, lotion, gel, spray or suspension. They may be either anhydrous or aqueous, depending on the clinical indication.

The compounds according to the invention are present in these pharmaceutical compositions in concentrations of between 0.1 and 10% by weight, and in particular of between 0.2 and 5% by weight.

The cosmetic compositions are, in particular, intended to be used in the form of a lotion, gel, soap, shampoo, aerosol or foam and contain, in a cosmetically acceptable excipient, at least one compound of formula (I) or one of its acid addition salts.

The concentration of these compounds of formula (I) in these compositions is preferably between 0.01 and 5% by weight and in particular between 0.05 and 3% by weight.

The compositions according to the invention may contain various additives customarily used in cosmetics or in pharmacy and in particular active substances such as hydrating agents, such as thiamorpholinone and its derivatives or urea; antiseborrheic agents, such as S-carboxymethylcysteine, S-benzylcysteamine and their derivatives; or thioxolone.

The compounds according to the invention may be combined with compounds which further improve their activity in respect of hair regrowth and/or retardation of hair loss, such as the following compounds:

nicotinic acid esters, and amongst these more particularly the $C_1$–$C_6$ alkyl nicotinates and in particular methyl nicotinate or benzyl nicotinate;

steroid and non-steroid anti-inflammatory agents well known in the state of the art, and in particular hydrocortisone, its salts and its derivatives, and niflumic acid;

retinoids, and more particularly t-transretinoic acid, which is also termed tretinoin, isotretinoin, retinol or vitamin A and its derivatives, such as the acetate, the palmitate or the propionate, or zinc motretinide, etretinate or t-trans-retinoate;

antibacterial agents chosen more particularly from macrolides, pyranosides and tetracyclines, and in particular erythromycin;

calcium antagonists, such as, more particularly, cinnarizine and diltiazem;

hormones, such as estriol or analogues or thyroxine and its salts;

antiandrogenic agents, such as oxendolone, spironolactone or diethylstilbestrol; and compounds which capture OH radicals, such as dimethyl sulphoxide.

Compounds such as diazoxide, corresponding to 3-methyl-7-chloro-2H-1,2,4-benzothiadiazine-1,1-dioxide; spiroxazone, or 7-(acetylthio)-4', 5'-dihydrospiro-[androst-4-ene-17,2'-(3'H)-furan]-3-one; phospholipids, such as lecithin; linoleic and linolenic acids; salicylic acid and its derivatives described in French Patent 2,581,542, and more particularly the salicylic acid derivatives carrying an alkanoyl group having 2 to 12 carbon atoms in the 5-position of the benzene ring; hydroxycarboxylic or ketocarboxylic acids and their esters, lactones and their corresponding salts; anthralin or 1,8,9-trihydroxyanthracene, carotenoids, and 5,8,11,14-eicosatetrainoic or 5,8,11-eicosatriinoic acids, their esters and amides may also be combined with the compounds of the invention, optionally in a mixture with the others.

The compounds according to the invention may also be combined with surfactants, and amongst these in particular those chosen from the nonionic and amphoteric surfactants.

Amongst the nonionic surfactants, those which will be mentioned are the polyhydroxypropyl ethers described, in particular, in French Patents Nos. 1,477,048; 2,091,516; 2,169,787; 2,328,763 and 2,574,786; the oxyethylenated (C$_8$–C$_9$)alkylphenols containing from 1 to 100 moles of ethylene oxide and preferably 5 to 35 moles of ethylene oxide; and the alkylpolyglycosides of formula:

$$C_nH_{2n+1}(C_6H_{10}O_5)_xH \qquad (A)$$

in which n varies from 8 to 15 inclusive and x from 1 to 10 inclusive.

Amongst the amphoteric surfactants, those which will be mentioned more particularly are the amphocarboxyglycinates and the amphocarboxypropionates defined in the CTFA Dictionary, 3rd edition, 1982, and sold, in particular, under the name MIRANOL ® by MIRANOL.

The compounds according to the invention may be introduced in excipients which further improve the activity in respect of regrowth, having, at the same time, advantageous properties in respect of cosmetic characteristics, such as ternary volatile mixtures of alkylene glycol alkyl ether, in particular C$_1$–C$_4$-alkylene glycol or dialkylene glycol C$_1$–C$_4$-alkyl ether, preferably C$_1$–C$_4$-dialkylene glycol C$_1$–C$_4$-alkyl ether, ethyl alcohol and water, the glycol solvent denoting more particularly ethylene glycol monoethyl ethers, propylene glycol monomethyl ether or diethylene glycol monomethyl ether.

The compounds according to the invention may also be introduced into gelled or thickened excipients, such as essentially aqueous excipients gelled by means of heterobiopolysaccharides, such as xanthan gum or cellulose derivatives, aqueous-alcoholic excipients gelled by means of polyhydroxyethyl acrylates or methacrylates, or essentially aqueous excipients thickened in particular by means of polyacrylic acids crosslinked by a polyfunctional agent, such as the Carbopols sold by GOODRICH.

These compositions may also contain preservatives, stabilisers, pH regulators, agents which modify the osmotic pressure, emulsifiers, UVA and UVB filters, and antioxidants, such as α-tocopherol, butylhydroxyanisole or butylhydroxytoluene.

The physiologically acceptable medium may consist of water or a mixture of water and a solvent or a mixture of solvents, the solvents being chosen from the cosmetically or pharmaceutically acceptable organic solvents and chosen more particularly from C$_1$–C$_4$ lower alcohols, such as ethyl alcohol, isopropyl alcohol or tert-butyl alcohol, alkylene glycols, alkylene glycol alkyl ethers and dialkylene glycol alkyl ethers, such as ethylene glycol monoethyl ether, propylene glycol monomethyl ether and diethylene glycol monomethyl ether. The solvents, when they are present, are present in proportions of between 1 and 80% by weight relative to the total weight of the composition.

The physiologically acceptable media may be thickened with the aid of thickeners customarily used in cosmetics or in pharmacy, and the heterobiopolysaccharides, such as xanthan gum, scleroglucans, cellulose derivatives, such as cellulose ethers, and acrylic polymers, which may or may not be crosslinked, may be mentioned more particularly.

The thickeners are preferably present in proportions of between 0.1 and 5% by weight and in particular between 0.4 and 3% by weight, relative to the total weight of the composition.

The invention also relates to a process for the cosmetic treatment of hair or the scalp, consisting in applying thereto at least one composition as defined above, with a view to improving the appearance of the hair.

Another subject of the invention consists in the use of the composition containing the compounds of formula (I) defined above, for the preparation of a medicament having the effect of inducing or stimulating hair growth and retarding hair loss.

The treatment consists in the main in applying the composition as defined above to the alopecic zones of the scalp of an individual.

The preferred method of application consists in applying 1 to 2 g of the composition to the alopecic zone at a rate of one to two applications per day, for 1 to 7 days per week and continuing this treatment for a period of 1 to 6 months.

The compositions may, in particular, be used in the treatment of pelade, hair loss and desquamative dermatites.

The following examples are intended to illustrate the invention without, however, having a limiting character.

PREPARATION EXAMPLES

EXAMPLE 1

2-Methyl-4-amino-6-piperidinopyrimidine 3-oxide

Part 1:
Preparation of 2-methyl-4-amino-6-chloropyrimidine 150 g (1.2 mol) of anhydrous 2-methyl-4-amino-6-hydroxypyrimidine are added little by little, with good stirring, to 720 ml of phosphorus oxychloride. The mixture is refluxed gently for 5 hours. A yellow solution is obtained. After cooling to 20° C., the precipitate formed is drained. An oily residue is recovered by evaporating the filtrate almost to dryness. This oily residue is poured, little by little, onto 500 g of ice, with stirring and while cooling the vessel in ice. The precipitate is introduced little by little into the solution obtained after some time. The addition is exothermic and the mixture must be cooled well in an ice bath. All of the solid dissolves. The solution is cooled to 0° C. and is rendered alkaline to pH 8 by the addition of 20% ammonia (850 ml). The formation becomes very thick. The solid is drained and washed on the filter with 100 ml of 10% aqueous sodium chloride solution and then with 200 ml of water. 144.2 g of crude product are obtained, which are recrystallised from acetonitrile. 97 g (0.676 mol) of pure product having a melting point of 191° C. are recovered. The yield of recrystallised product is 56.3%.

Elementary analysis for C$_5$H$_6$N$_3$Cl; molecular weight = 143.5.

|  | C | H | N | Cl |
|---|---|---|---|---|
| Calculated | 41.81 | 4.18 | 29.27 | 24.74 |
| Found | 41.70 | 4.25 | 29.39 | 24.64 |

The mass and $^{13}$C NMR spectra are in accordance with the expected structure.

Part 2:
Preparation of 2-methyl-4-amino-6-chloropyrimidine 3-oxide 50.23 g (0.35 mol) of 2-methyl-4-amino-6-chloropyrimidine are partially dissolved in 700 ml of methanol. The mixture is cooled to 0° C. and 131.7 g (0.42 mol) of approximately 55% m-chloroperbenzoic acid are introduced, in small fractions, with good stirring, at a rate such that the temperature remains below 5° C. After the end of the introduction, the mixture is kept below 5° C. for a further 3 hours and is then allowed to return to ambient temperature. After 4 hours at 20° C., only traces of starting material still remain. The mixture is left to freeze overnight. The following day the precipitate is drained and washed with 30 ml of cold methanol. The precipitate is taken up in 120 ml of iced methanol, with stirring. The solid is drained and dried. 27.4 g of pure product having a melting point of 191° C. are obtained.

A second fraction is recovered by concentrating the methanolic mother liquors to about 200 ml. The precipitate is drained, washed with 10 ml of cold methanol and then taken up in 250 ml of ethyl ether, with stirring, in order to remove the m-chlorobenzoic acid which it contains, and finally in 25 ml of cold methanol. 5.43 g of pure product having a melting point of 191° C. are thus recovered. The total yield is 58.8%.

Elementary analysis for $C_5H_6N_3OCl$; molecular weight=159.5.

|  | C | H | N | O | Cl |
|---|---|---|---|---|---|
| Calculated with 0.5 m $H_2O$ | 35.61 | 4.15 | 24.92 | 14.24 | 21.07 |
| Found | 33.15 | 4.26 | 24.82 | 14.88 | 20.80 |

The mass and $^{13}C$ NMR spectra are in accordance with the expected structure.

Part 3:

Preparation of 2-methyl-4-amino-6-piperidinopyrimidine 3-oxide

A solution of 44 g (0.261 mol) of 2-methyl4-amino-6-chloropyrimidine 3-oxide in 352 ml of piperidine is refluxed gently for 4 hours 30 minutes, with stirring and under nitrogen. A yellow suspension is obtained. The suspension is cooled in a salt ice bath and the precipitate is drained and washed on the filter with 30 ml of piperidine and then with ethyl ether. It is then taken up, with stirring, twice ill 150 ml of ice-water. The solid is drained and dried under vacuum at ambient temperature. 42 g of product in the form of the monohydrate are obtained. The product is recrystallized from acetonitrile with 3% of water, After drying at 80° C., 37.8 g (0.181 mol) of anhydrous pure product having a melting point of 200°-200.5° C. are recovered. The yield is 69.6%.

Elementary analysis for $C_{10}H_{16}N_4O$; molecular weight=208.

|  | C | H | N | O |
|---|---|---|---|---|
| Calculated | 57.69 | 7.69 | 26.92 | 7.69 |
| Found | 57.60 | 7.79 | 26.93 | 7.89 |

The mass and $^{13}C$ NMR spectra are in accordance with the expected structure.

EXAMPLE 2

2-Methyl-4-amino-6-dimethylaminopyrimidine 3-oxide

METHOD:

2 g ($1.254 \times 10^{-2}$ mol) of 2-methyl-4-amino6-chloropyrimidine 3-oxide, prepared in accordance with part 2 of Example 1, in suspension in 20 ml of a 33% ethanolic solution of dimethylamine are placed in a 50 ml three-necked flask fitted with a condenser, a thermometer and a magnetic stirrer. The reaction mixture is stirred for 6 hours at 30° C. It is cooled to 5° C. and 50 ml of a 10% alcohol solution of potassium hydroxide are then added. The mixture is stirred for 1 hour. It is filtered on a glass frit previously filled with silica. The solution obtained is evaporated to dryness. The precipitate is recrystallised from an acetonitrile/water (99.5/0.5) mixture. Mass obtained: 1.56 g.

Yield: 74% m.p.: 215° C.

Elementary analysis for $C_7H_{12}N_4O$; molecular weight=168.

|  | C | H | N | O |
|---|---|---|---|---|
| Calculated with 0.2 mol of water | 48.95 | 7.22 | 32.63 | 11.18 |
| Found | 48.99 | 7.15 | 32.69 | 10.95 |

The $^1H$ and $^{13}C$ NMR and mass spectra are in accordance with the expected structure.

EXAMPLE 3

2-Methyl-4-amino-6-diethylaminopyrimidine 3-oxide

METHOD:

3 g ($1.88 \times 10^{-2}$ mol) of 2-methyl-4-amino6-chloropyrimidine 3-oxide, prepared in accordance with part 2 of Example 1, in suspension in 30 ml of diethylamine are placed in a 50 ml three-necked flask fitted with a condenser, a thermometer, a magnetic stirrer and an argon inlet. The reaction mixture is stirred under an argon atmosphere for 4 days at 55° C. The reaction mixture is evaporated to dryness and the residue is them chromatographed on silica gel using an ethyl acetate/methanol elution gradient. After evaporation, a solid crude product is obtained which is recrystallised from an acetonitrile/water (99.5/0.5) mixture.

Yield: 15% m.p.: 143° C.

Elementary analysis for $C_9H_{16}N_4O$; molecular weight=196.

|  | C | H | N | O |
|---|---|---|---|---|
| Calculated with 0.22 mol of water | 54.00 | 8.22 | 28.00 | 9.77 |
| Found | 54.03 | 8.21 | 28.08 | 9.52 |

The $^1H$ NMR and mass spectra are in accordance with the expected structure.

EXAMPLE 4

2-Methyl-4-amino-6-morpholinopyrimidine 3-oxide

Following the method described in Example 3, using morpholine.

Temperature: 90° C.

Time: 4 hours 30 minutes.

Recrystallisation from an acetonitrile/water (99/1) mixture.

Yield: 23%.

m.p.: 203° C.

Elementary analysis for $C_9H_{14}N_4O_2$; molecular weight=210.

|  | C | H | N | O |
|---|---|---|---|---|
| Calculated with 0.44 mol of water | 49.54 | 6.82 | 25.69 | 17.94 |

|       | C     | H    | N     | O     |
|-------|-------|------|-------|-------|
| Found | 49.60 | 6.74 | 25.86 | 18.15 |

The $^1$H NMR and mass spectra are in accordance with the expected structure.

EXAMPLE 5

2-Methyl-4-amino-6-(N-methylpiperazino)pyrimidine 3-oxide

Following the method described in Example 3, with N-methylpiperazine.
Temperature: 70° C.
Time: 3 hours 30 minutes.
Recrystallisation from an acetonitrile/water (97/3) mixture.
Yield: 35%.
m.p.: 200° C.
Elementary analysis for $C_{10}H_{17}N_5O$; molecular weight=223.

|                                | C     | H    | N     | O    |
|--------------------------------|-------|------|-------|------|
| Calculated for 0.05 mol of water | 53.59 | 7.64 | 31.26 | 7.50 |
| Found                          | 53.59 | 7.66 | 31.43 | 7.29 |

The $^1$H NMR and mass spectra are in accordance with the expected structure.

EXAMPLE 6

2-Methyl-4-amino-6(n-butylamino)pyrimidine 3-oxide

METHOD:

3 g ($1.88 \times 10^{-2}$ mol) of 2-methyl-4-amino-6-chloropyrimidine 3-oxide, prepared in accordance with part 2 of Example 1, and 7.53 g (4 eq) of potassium bicarbonate suspended in 30 ml of ethanol are placed in a 50 ml three-necked flask fitted with a condenser, a thermometer, a magnetic stirrer and an argon inlet. The reaction mixture is stirred under an argon atmosphere and 3.7 ml (2 eq) of butylamine are introduced. The mixture is heated under ethanol reflux for 24 hours. The reaction mixture is evaporated to dryness and the residue is then taken up in 20 ml of water. The mixture is cooled to 0° C. and filtered on a glass frit. 2.6 g of crude product are obtained. The precipitate is dissolved in an ethyl acetate/methanol (80/20) mixture. 2 g of silica are added per gram of product and the mixture is stirred for 30 minutes. It is filtered and the filtrate is evaporated to dryness. The precipitate is recrystallised from an acetonitrile/water (70/30) mixture.
Yield: 21%.
m.p.: 222° C.
Elementary analysis for $C_9H_{16}N_4O$; molecular weight=196.

|        | C     | H    | N     | O    |
|--------|-------|------|-------|------|
| Theory | 55.10 | 8.16 | 28.57 | 8.16 |
| Found  | 55.08 | 8.21 | 28.54 | 8.35 |

The $^1$H NMR and mass spectra are in accordance with the expected structure.

EXAMPLE 7

2-Methyl-4-amino-6-benzylaminopyrimidine 3-oxide

Following the method described in Example 6, with benzylamine.
Temperature: ethanol reflux.
Time: 27 hours 30 minutes.
Recrystallisation from an acetonitrile/water (97/3) mixture.
Yield: 21%.
m.p.: 210° C.
Elementary analysis for $C_{12}H_{14}N_4O$; molecular weight=230.

|        | C     | H    | N     | O    |
|--------|-------|------|-------|------|
| Theory | 62.60 | 6.09 | 24.34 | 6.95 |
| Found  | 62.47 | 6.12 | 24.48 | 7.00 |

The $^1$H NMR and mass spectra are in accordance with the expected structure.

EXAMPLE 8

2-Methyl-4-amino-6-anilinopyrimidine 3-oxide

Following the method described in Example 6, with aniline.
Temperature: ethanol reflux.
Time: 3 days 18 hours.
Recrystallisation from an acetonitrile/water (99/1) mixture.
Yield: 14%.
m.p.: 241° C.
Elementary analysis for $C_{11}H_{12}N_4O$; molecular weight=216.

|                                | C     | H    | N     | O    |
|--------------------------------|-------|------|-------|------|
| Calculated for 0.2 mol of water | 60.10 | 5.64 | 25.50 | 8.74 |
| Found                          | 60.06 | 5.75 | 25.47 | 8.44 |

The $^1$H NMR and mass spectra are in accordance with the expected structure.

EXAMPLE 9

2-Methyl-4-amino-6-ethoxypyrimidine 3-oxide

METHOD:

0.48 g of sodium are dissolved in 45 ml of ethanol in a 100 ml three-necked flask fitted with a condenser, a thermometer, a magnetic stirrer and an argon inlet. 3 g ($1.88 \times 10^{-2}$ mol) of 2-methyl-4-amino-6-chloropyrimidine 3-oxide, prepared in accordance with part 2 of Example 1, are added and the reaction mixture is refluxed for 25 hours 30 minutes. The heterogeneous mixture is evaporated to dryness. The residue is purified on a silica gel column using an elution gradient with ethyl acetate/methanol. After evaporation, a solid crude product is obtained which is recrystallised from acetonitrile.
Yield: 23%.
m.p.: 157° C.
Elementary analysis for $C_7H_{11}N_3O_2$; molecular weight=169.

|        | C     | H    | N     | O     |
|--------|-------|------|-------|-------|
| Theory | 49.70 | 6.51 | 24.85 | 18.93 |

|       | C     | H    | N     | O     |
|-------|-------|------|-------|-------|
| Found | 49.64 | 6.57 | 24.95 | 18.94 |

The hu 1H and $^{13}$C NMR and mass spectra are in accordance with the expected structure.

EXAMPLE 10

2-Methyl-4-amino-6-(2,4-dimethylphenyl)oxypyrimidine 3-oxide

Following the method described in Example 9, with 2,4-dimethylphenol.

Temperature: 75° C.
Time: 24 hours.
Recrystallisation from acetonitrile.
Yield: 37%.
m.p.: 159° C.

Elementary analysis for $C_{13}H_{15}N_3O_2$; molecular weight=245.

|        | C     | H    | N     | O     |
|--------|-------|------|-------|-------|
| Theory | 63.67 | 6.12 | 17.14 | 13.06 |
| Found  | 63.52 | 6.17 | 17.18 | 13.30 |

The $^1$H and $^{13}$C NMR and mass spectra are in accordance with the expected structure.

EXAMPLE 11

2-Methyl-4-amino-6-(1-methyl)ethoxypyrimidine 3-oxide

Part 1:
Preparation of 2-methyl-4-amino-6-(1-methyl)ethoxypyrimidine.
METHOD:

1.8 g of sodium are dissolved in 150 ml of isopropanol in a 250 ml three-necked flask fitted with a condenser, a thermometer, an argon inlet and a magnetic stirrer. 10 g ($6.97 \times 10^{-2}$ mol) of 2-methyl-4-amino6-chloropyrimidine, prepared in accordance with part 1 of Example 1, are added and the reaction mixture is refluxed under argon for 24 hours. The heterogeneous mixture is evaporated to dryness. The solid residue is dissolved in a minimum of ethyl acetate and the solution is then filtered on a glass frit previously filled with silica. The filtrate is then evaporated to dryness. The precipitate is taken up in ice-petroleum ether. 5.1 g are obtained.

Yield: 44%.
m.p.: 106° C.

Elementary analysis for $C_8H_{13}N_3O$; molecular weight=167.

|                                 | C     | H    | N     | O     |
|---------------------------------|-------|------|-------|-------|
| Calculated for 0.08 mol of water | 56.97 | 7.81 | 24.92 | 10.28 |
| Found                           | 57.04 | 7.86 | 25.04 | 10.20 |

The $^1$H and $^{13}$C NMR and mass spectra are in accordance with the expected structure.

Part 2:
Preparation of 2-methyl-4-amino-6-(1-methyl)ethoxypyrimidine 3-oxide.
METHOD:

2 g ($1.2 \times 10^{-2}$ mol) of 2-methyl-4-amino6-(1-methyl)ethoxypyrimidine in suspension in 30 ml of ethanol are placed in a 50 ml three-necked flask fitted with a condenser, a thermometer and a magnetic stirrer. The mixture is cooled to 0° C. and metachloroperbenzoic acid (2 eq) is added in small spatulas. The reaction mixture is stirred for 4 hours at between 0° and 5° C. The reaction mixture is purified on a silica gel column using an elution gradient with ethyl acetate/methanol. After evaporation, a solid crude product is obtained which is recrystallised from toluene.

Yield: 65%.
m.p.: 140° C.

Elementary analysis for $C_8H_{13}N_3O_2$: molecular weight=183.

|                                | C     | H    | N     | O     |
|--------------------------------|-------|------|-------|-------|
| Calculated for 0.2 mol of water | 51.44 | 7.18 | 22.51 | 18.86 |
| Found                          | 51.51 | 7.30 | 22.62 | 18.45 |

The $^1$H and $^{13}$C NMR and mass spectra are in accordance with the expected structure.

EXAMPLE 12

2-Methyl-4-amino-6-butoxypyrimidine 3-oxide

Part 1
Preparation of 2-methyl-4-amino-6-butoxypyrimidine

Following the method described in part 1 of Example 11, with butanol.

Temperature: 90° C.
Time: 3 hours.
Recrystallisation from a petroleum ether/acetone mixture.
Yield: 69%.
m.p.: 92° C.

Elementary analysis for $C_9H_{15}N_3O$; molecular weight=181.

|        | C     | H    | N     | O    |
|--------|-------|------|-------|------|
| Theory | 59.67 | 8.29 | 23.20 | 8.84 |
| Found  | 59.94 | 8.31 | 23.29 | 9.02 |

The $^1$H NMR and mass spectra are in accordance with the expected structure.

Part 2:
Preparation of 2-methyl-4-amino-6-butoxypyrimidine 3-oxide

Following the method described in part 2 of Example 11, with 2-methyl-4-amino-6-butoxypyrimidine.

Temperature: 0°-10° C.
Time: 6 hours.
Recrystallisation from cyclohexane.
Yield: 46%.
m.p.: 94° C.

Elementary analysis for $C_9H_{15}N_3O_2$; molecular weight=197.

|                                 | C     | H    | N     | O     |
|---------------------------------|-------|------|-------|-------|
| Calculated for 0.4 mol of water | 52.88 | 7.74 | 20.56 | 18.80 |
| Found                           | 52.83 | 8.00 | 20.61 | 18.77 |

The $^1$H and $^{13}$C NMR and mass spectra are in accordance with the expected structure.

EXAMPLE 13

2-Methyl-4-ethoxycarbonylamino-6-piperidinopyrimidine 3-oxide

METHOD:

2 g ($9.6 \times 10^{-3}$ mol) of 2-methyl-4-amino-6-piperidinopyrimidine 3-oxide in suspension in 20 ml of dichloromethane previously dried over a molecular sieve are placed in a 50 ml three-necked flask fitted with a condenser, a thermometer, a magnetic stirrer and a dropping funnel. 1.1 equivalent of triethylamine, which is 1.5 ml, are added. The reaction mixture is cooled to 0° C. and 1.1 equivalents of ethyl chloroformate, which is 1 ml, are added dropwise. The mixture is allowed to return to ambient temperature (20° C.) and is stirred for 4 hours. 10 ml of water are added to the reaction mixture. The organic phase is extracted with:

10 ml of 1% hydrochloric acid.
10 ml of a 1% sodium carbonate solution.
2×10 ml of water.

and then dried over sodium sulphate. After filtering through paper, the solution is evaporated. A white precipitate is obtained. Mass obtained=1.8 g. This precipitate is recrystallised from 9 ml of water. Mass obtained: 1.4 g.

Yield: 52%.
m.p.: 134° C.

Elementary analysis for $C_{13}H_{20}N_4O_3$; molecular weight=280.

|        | C     | H    | N     | O     |
|--------|-------|------|-------|-------|
| Theory | 55.71 | 7.14 | 20.00 | 17.14 |
| Found  | 55.75 | 7.21 | 20.16 | 17.34 |

The $^1H$ and $^{13}C$ NMR and mass spectra are in accordance with the expected structure.

EXAMPLE 14

Inner salt of 2-methyl-4-amino-6-piperidino-3-sulphoxypyrimidinium hydroxide

1st Method:

0.666 ml (0.01 mol) of chlorosulphonic acid is added, with stirring, to a solution of 3.42 ml (0.02 mol) of N,N-diisopropylethylamine in 25 ml of chloroform cooled in ice. After a waiting time of 30 minutes, 1.04 g (0.005 mol) of 2-methyl-4-amino-6-piperidinopyrimidine 3-oxide prepared according to Example 1 are added and the mixture is kept at 15°–20° C. for 4 hours 30 minutes under nitrogen. The solution is evaporated. The residue, taken up in a little water, allows a white product to crystallise, which is filtered off. After recrystallisation from a DMF/water mixture, 1.3 g of pure inner salt, which decomposes at 235° C., are obtained. The yield is 90.2%.

Elementary analysis for $C_{10}H_{16}N_4O_4S$; molecular weight=288.

|            | C     | H    | N     | O     | S     |
|------------|-------|------|-------|-------|-------|
| Calculated | 41.66 | 5.55 | 19.45 | 22.22 | 11.11 |
| Found      | 41.49 | 5.59 | 19.46 | 22.11 | 11.08 |

The mass and $^1H$ NMR spectra are in accordance with the expected structure.

2nd Method:

3.18 g (0.02 mol) of sulphur trioxide/pyridine complex are added, with stirring, to a suspension of 1.04 g (0.005 mol) of 2-methyl-4-amino-6-piperidinopyrimidine 3-oxide in 15 ml of DMF. The mixture is kept at ambient temperature for 6 hours. The solution obtained is diluted with 60 g of ice-water. The white precipitate obtained is filtered off and washed with ice-water. After recrystallisation from a DMF/water mixture, 1.1 g of pure inner salt, which decomposes at 235° C., are obtained. The yield is 76.4 %.

EXAMPLE 15

Inner salt of 2-methyl-4-amino-6-dimethylamino-3-sulphoxypyrimidinium hydroxide.

0.133 ml (0.002 mol) of chlorosulphonic acid is added, with stirring, to a solution of 0.72 ml (0.0042 mol) of N,N-diisopropylethylamine in 12 ml of a 1/1 chloroform/dimethylformamide mixture, cooled in ice. After a waiting time of 30 minutes, 0.168 g (0.001 mol) of 2-methyl-4-amino-6-dimethylaminopyrimidine 3-oxide prepared according to Example 2 is added and the mixture is kept at between 5° and 10° C. for 7 hours under nitrogen. The solvent is evaporated. The residue, taken up in a little water, allows a white product to crystallise, which is filtered off. After recrystallisation from a DMF/water mixture, 0.11 g of pure inner salt, which decomposes at 226° C., is obtained. The yield is 44.3%. Elementary analysis for $C_7H_{12}N_4O_4S$; molecular weight=248.

|            | C     | H    | N     | O     | S     |
|------------|-------|------|-------|-------|-------|
| Calculated | 33.87 | 4.84 | 22.58 | 25.81 | 12.90 |
| Found      | 33.90 | 4.90 | 22.67 | 26.00 | 12.84 |

The mass and $^1H$ NMR spectra are in accordance with the expected structure.

EXAMPLE 16

2,4-Dimethyl-6-piperidinopyrimidine 3-oxide

Part 1:

Preparation of 2,4-dimethyl-6-chloropyrimidine.

METHOD:

20 g ($16.1 \times 10^{-2}$ mol) of 2,4-dimethyl-6-hydroxypyrimidine in suspension in 150 ml of phosphorus oxychloride are introduced into a 250 ml three-necked flask fitted with a thermometer, a condenser and a magnetic stirrer. The mixture is heated at 90° C. for one and a half hours. The mixture is then cooled and then evaporated to dryness. The residue which crystallises at ambient temperature is added, in small portions, to a binary mixture consisting of dichloromethane (200 ml) and 10% ammonia (300 ml), previously cooled to −5° C. in an ice bath containing sodium chloride. The mixture is stirred cold for half an hour and the organic phase is then decanted off, washed with water until neutral and then dried over sodium sulphate, filtered and evaporated. The yellow liquid obtained is filtered through a glass frit filled with silica using the dichloromethane/methanol (99/1) eluent system; the pure fractions collected are evaporated. 16.4 g of a colourless liquid which has a persistent odour and which crystallises in a refrigerator are obtained.

Yield: 71%.

Elementary analysis for $C_6H_7ClN_2$; molecular weight=142.5.

|  | C | H | N | Cl |
|---|---|---|---|---|
| Calculated | 50.53 | 4.91 | 19.65 | 24.91 |
| Found | 50.61 | 4.88 | 19.55 | 24.94 |

The $^1$H and $^{13}$C NMR and mass spectra are in accordance with the expected structure.

Part 2:

Preparation of 2,4-dimethyl-6-chloropyrimidine 3-oxide 20 g ($14.03 \times 10^{-2}$ mol) of 2,4-dimethyl-6-chloropyrimidine are dissolved in 300 ml of dichloromethane in a 500 ml three-necked flask fitted with a thermometer and a magnetic stirrer. The mixture is cooled to 5° C. and 65.3 g of 55% metachloroperbenzoic acid, which is about 1.5 equivalents, are then added in solid portions. The reaction mixture is then stirred for 24 hours at ambient temperature (25° C.) and then filtered through a 3 frit. The filtrate is washed with 150 ml of a 6% aqueous sodium hydroxide solution and then with $2 \times 50$ ml of water to render neutral. It is then dried over sodium sulphate and then filtered through paper and evaporated. The crude mass is recrystallised from n-hexane.

Mass obtained: 10.89 g.
Yield: 49%.
m.p.: 100° C.

Elementary analysis for $C_6H_7N_2OCl$; molecular weight=158.

|  | C | H | N | O | Cl |
|---|---|---|---|---|---|
| Calculated with 0.8 mol of $H_2O$ | 45.00 | 4.48 | 17.50 | 10.83 | 22.18 |
| Found | 45.07 | 4.42 | 17.59 | 10.97 | 22.15 |

The $^{13}$C NMR spectrum and the mass spectrum are in accordance with the expected structure.

Part 3:

Preparation of 2,4-dimethyl-6-piperidinopyrimidine 3-oxide 100 ml of piperidine are introduced into a 250 ml three-necked flask fitted with a thermometer, a condenser and a magnetic stirrer and 13.5 g ($8.51 \times 10^{-2}$ mol) of 2,4-dimethyl-6-chloropyrimidine 3-oxide are then added, in solid portions, in a manner such that exothermic heat does not develop beyond 60° C. The reaction mixture is then allowed to return to ambient temperature; the piperidinium hydrochloride is then removed from the mixture by filtration and the filtrate is evaporated to dryness. The crude oil obtained crystallises rapidly at ambient temperature. The crystalline mass is dissolved in a minimum of ethanol and ethyl ether is then added cold until precipitation occurs. The mixture is stirred for half an hour and the precipitate is then filtered off and drained. A final filtration through silica gel using the dichloromethane/methanol (90/10) eluent system allows white crystals to be obtained.

Mass obtained: 6.5 g.
Yield: 37%.
m.p.: 137° C.

Elementary analysis for $C_{11}H_{17}N_3O$; molecular weight=207.

|  | C | H | N | O |
|---|---|---|---|---|
| Calculated with 0.1 mol of $H_2O$ | 63.21 | 8.23 | 20.11 | 8.52 |
| Found | 63.19 | 8.20 | 20.01 | 8.57 |

The $^1$H and $^{13}$C NMR and mass spectra are in accordance with the expected structure.

EXAMPLE 17

Inner salt of 2,4-dimethyl-6-piperidino-3-sulphoxypyrimidinium hydroxide

Following the procedure of the first method described in Example 14, using 1.035 g of 2,4-dimethyl6-piperidinopyrimidine 3-oxide prepared in accordance with Example 16.

The reaction time is 2 hours 30 minutes and the temperature is kept between 0° C. and 5° C. The product obtained, recrystallised from a dimethylformamide/water mixture, decomposes at 202° C.

The yield is 69.6%. Elementary analysis for $C_{11}H_{37}N_3O_4S$; molecular weight=287.

|  | C | H | N | O | S |
|---|---|---|---|---|---|
| Calculated with 0.16 m of $H_2O$ | 45.53 | 5.97 | 14.49 | 22.96 | 11.04 |
| Found | 45.60 | 5.98 | 14.41 | 22.96 | 11.10 |

The mass and $^1$H NMR spectra are in accordance with the expected structure.

EXAMPLE 18

2,4-Dimethyl-6-ethoxypyrimidine 3-oxide

METHOD:

0.32 g (1.1 eq) of sodium are dissolved in 30 ml of absolute ethanol in a 50 ml three-necked flask fitted with a condenser, a thermometer, a magnetic stirrer and an argon inlet. 2 g (0.0126 mol) of 2,4-dimethyl6-chloropyrimidine 3-oxide, prepared in accordance with part 2 of Example 16, are added and the mixture is stirred at ambient temperature for 2 hours 15 minutes. The reaction mixture is neutralised with ethanol containing hydrochloride. The mixture is evaporated to dryness. The residue is purified on a silica gel column using an ethyl acetate/methanol mixture as the eluent. After evaporation, a solid crude product is obtained which is recrystallised from hexane.

Yield: 81%.
m.p.: 101° C.

Elementary analysis for $C_8H_{12}N_2O_2$; molecular weight=168.

|  | C | H | N | O |
|---|---|---|---|---|
| Theory | 57.14 | 7.14 | 16.67 | 19.05 |
| Found | 57.09 | 7.20 | 16.57 | 19.01 |

The mass and $^1$H NMR spectra are in accordance with the expected structure.

COMPOSITION EXAMPLE 1

The following composition is prepared:

| 2,4-dimethyl-6-piperidino-pyrimidine 3-oxide |  | 5.0 g |
|---|---|---|
| Propylene glycol | 22.8 g | |
| Ethyl alcohol | 55.1 g | 95.0 g |

-continued

| | |
|---|---|
| Water qs | 100.0 g |

This composition is in the form of a lotion.

1 to 2 g of this composition are applied to the alopecic zones of the scalp, optionally accompanied by a massage to promote its penetration, using one to two applications per day for a treatment period of three months.

COMPOSITION EXAMPLE 2

The following composition is prepared:

| | | |
|---|---|---|
| 2-methyl-4-amino-6-piperidino-pyrimidine 3-oxide | 8.5 g | |
| Propylene glycol | 22.8 g | |
| Ethyl alcohol | 55.1 g | 91.5 g |
| Water qs | 100.0 g | |

This composition is in the form of a lotion.

COMPOSITION EXAMPLE 3

A lotion of the following composition is prepared:

| | | |
|---|---|---|
| 2-methyl-4-amino-6-piperidino-pyrimidine 3-oxide | 6.0 g | |
| Ethyl alcohol | 50.0 g | 94.0 g |
| Water qs | 100.0 g | |

1 to 2 ml of these lotions are applied to the alopecic zones of the scalp; these applications, optionally accompanied by a massage to promote penetration, being carried out once or twice per day.

COMPOSITION EXAMPLE 4

The following composition is prepared:

| | | |
|---|---|---|
| 2-methyl-4-amino-6-piperidino-pyrimidine 3-oxide | 4.0 g | |
| Propylene glycol | 6.45 g | |
| Absolute ethanol qs | 100.0 g | 96.0 g |

This composition is in the form of a lotion.

We claim:

1. A composition comprising in a physiologically acceptable medium, an effective amount of at least one compound corresponding to formula (I):

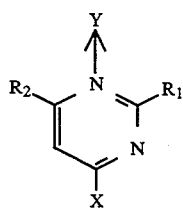

(I)

in which:

$R_1$ denotes a hydrogen atom or a $C_1$–$C_8$ saturated straight-chain alkyl radical;

$R_2$ denotes a $C_1$–$C_8$ saturated straight-chain alkyl radical, an —$NHR_3$ group in which $R_3$ denotes a hydrogen atom, or the group —$COOR_4$, where $R_4$ represents a $C_1$–$C_{12}$ straight-chain alkyl radical;

X denotes:
(i) a

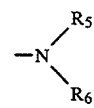

group
in which:

$R_5$ and $R_6$, which may be identical or different, denote a hydrogen atom, a straight-chain or branched $C_1$–$C_{12}$ alkyl group, which may be substituted by one or more halogen atoms, a $C_2$–$C_{12}$ straight-chain alkenyl group, a $C_3$–$C_{10}$ cycloalkyl group or an aryl or aralkyl group corresponding to the formula:

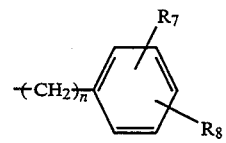

where n ranges from 0 to 4; and $R_7$ and/or $R_8$, independently of one another, denote a hydrogen atom, a $C_1$–$C_6$ lower alkyl or alkoxy group or a trifluoromethyl radical; or $R_5$ and $R_6$, together with the nitrogen atom to which they are bonded, form a saturated or unsaturated heterocycle selected from the group consisting of aziridinyl, azetidinyl, pyrrolidinyl, piperidyl, hexamethyleneimino, heptamethyleneimino, octamethyleneimino, tetrahydropyridinyl, dihydropyridyl, pyrrolyl, pyrazolyl, imidazolyl, triazolyl, 4-alkylpiperazinyl, morpholino and thiomorpholino;

(ii) an —$OR_9$ group, in which $R_9$ denotes a straight-chain or branched $C_1$–$C_{12}$ alkyl radical, which is optionally substituted by one or more halogen atoms, a $C_2$–$C_{12}$ alkenyl radical, $C_3$–$C_{10}$ cycloalkyl radical, a $C_7$–$C_{12}$ aralkyl radical or a phenyl radical, which is optionally substituted by one or two groups which, independently of one another, denote a $C_2$–$C_6$ alkyl radical, a $C_1$–$C_6$ alkoxy radical, a halogen atom or a trifluoromethyl radical; or (iii) an $SR_{10}$ group, in which $R_{10}$ has one of the same meanings as $R_9$; and Y denotes an oxygen atom or an —$OSO_3^\ominus$ group; or a physiologically acceptable acid addition salt thereof.

2. A composition according to claim 1, wherein $R_1$ and $R_2$ denote a methyl radical, and X denotes piperidyl; or $R_1$ denotes methyl, and $R_2$ denotes —$NHR_3$, in which $R_3$ has the same meaning as indicated in claim 1, and X denotes dimethylamino, diethylamino, n-butylamino, piperidyl, morpholino, 4-methylpiperazinyl, benzylamino or anilino.

3. A composition according to claim 1, wherein $R_1$ and $R_2$ denote methyl, and X represents the ethoxy group; or $R_1$ denotes methyl, and $R_2$ denotes —$NHR_3$, in which $R_3$ has the same meaning mentioned in formula (I), and X denotes the ethoxy, butoxy, 1-methylethoxy or 2,4-dimethylphenoxy group.

4. A pharmaceutical or cosmetic composition according to claim 1 in topical application form.

5. A composition according to claim 4, in the form of a pharmacutically acceptable ointment, dye, cream, pomade, powder, patch, impregnated buffer, vesicular solution, emulsion or dispersion, lotion, gel, spray or suspension, which is anhydrous or aqueous.

6. A pharmaceutical composition according to claim 5, wherein the compound of formula (I) is present in a concentration of between 0.1 and 10% by weight relative to the total weight of the composition.

7. A composition according to the claim 1 and which is useful in cosmetics, in the form of a lotion, gel, soap, shampoo, aerosol or foam and contains, in a cosmetically acceptable excipient, the at least one compound in a concentration of between 0.01 and 5% by weight.

8. A composition according to claim 4 which also contains a hydrating agent and an antiseborrheic agent.

9. A process for the cosmetic treatment of hair or the scalp, which comprises applying a composition as defined in claim 1 thereto.

10. A composition according to claim 1 which also contains a nicotinic acid ester, a steroid or non-steroid anti-inflammatory agent, a retinoid, an antibacterial agent, a calcium antagonist, a hormone, an antiandrogenic agent or a compound which captures OH radicals.

11. A composition according to claim 1, which also contains a diazoxide, a spiroxazone, a phospholipid, linoleic acid, linolenic acid, salicylic acid or a derivative thereof, a hydroxycarboxylic or ketocarboxylic acid, an ester, lactone or a salt or either, anthralin, a carotenoid, 5,8,11,14-eicosatetrainoic acid, an ester or amide thereof, and 5,8,11-eicosatriinoic acid, and an ester or amide thereof.

12. A composition according to claim 4 which also contains a nonionic or amphoteric surfactant.

13. A composition according to claim 4 which the physiologically acceptable medium consists of water, a mixture of water and one or more organic solvents or a mixture of organic solvents. the organic solvents being pharmaceutically or cosmetically acceptable.

14. A composition according to claim 13, wherein each organic solvent is a $C_1-C_4$ lower alcohol, an alkylene glycol, a monoalkylene glycol alkyl ethers or a dialkylene glycol alkyl ether.

15. A composition according to claim 4 wherein the physiologically acceptable medium comprises a thickening amount of thickener and/or gelling agent and contains a member selected from the group consisting of a preservative, a stabiliser, a pH regulator, an agent to modify the osmotic pressure, an emulsifier, a UVA filter, a UVB filter and an antioxidant.

16. A compound corresponding to the following formula:

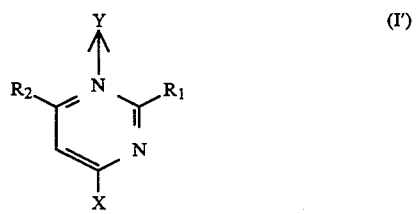

in which:
$R_1$ denotes a hydrogen atom or a $C_1-C_8$ saturated straight-chain alkyl radical;

$R_2$ denotes a $C_1-C_8$ saturated straight-chain alkyl radical, an —$NHR_3$ group in which $R_3$ denotes a hydrogen atom, or the group —$COOR_4$, where $R_4$ represents a $C_1-C_4$ straight-chain alkyl radical;

Y denotes an oxygen atom or the $OSO_3^\ominus$ group;

X denotes:
(i) a

group
in which:
$R_5$ and $R_6$, which may be identical or different, denote a hydrogen atom, a straight-chain or branched $C_1-C_{12}$ alkyl group, which may be substituted by one or more halogen atoms, a $C_2-C_{12}$ straight-chain alkenyl group, a $C_3-C_{10}$ cycloalkyl group or an aryl or aralkyl group corresponding to the formula:

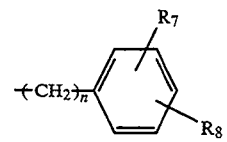

where
n ranges from 0 to 4; and
$R_7$ and/or $R_8$, independently of one another, denote a hydrogen atom, a $C_1-C_6$ lower alkyl or alkoxy group or a trifluoromethyl radical; or $R_5$ and $R_6$, together with the nitrogen atom to which they are bonded, form a saturated or unsaturated heterocycle selected from the group consisting of aziridinyl, azetidinyl, pyrrolidinyl, piperidyl, hexamethyleneimino, heptamethyleneimino, octamethyleneimino, tetrahydropyridinyl, dihydropyridyl, pyrrolyl, pyrazolyl, imidazolyl, triazolyl, 4-alkylpiperazinyl, morpholino and thiomorpholino; with the proviso that:

when Y denotes an oxygen atom, $R_1$ and $R_2$ denote, independently of one another, a $C_1-C_8$ saturated straight-chain alkyl radical and do not simultaneously denote the methyl radical when X denotes dimethylamino; and when Y denotes an $OSO_3^\ominus$ group $R_2$ does not denote —$NH_2$;

(ii) an —OR, group, in which $R_9$ denotes a straight-chain or branched $C_1-C_2$ alkyl radical, which is optionally substituted by one or more halogen atoms, a $C_2-C_{12}$ alkenyl radical, a $C_3-C_{10}$ cycloalkyl radical, a $C_7-C_{12}$ aralkyl radical or a phenyl radical, which is optionally substituted by one or two groups which, independently of one another, denote a $C_1-C_6$ alkyl radical, a $C_1-C_6$ alkoxy radical, a halogen atom or a trifluoromethyl radical; or when Y denotes an oxygen atom, $R_2$ denotes an —$NHR_3$ group as defined above;

(iii) an $SR_{10}$ group, in which $R_{10}$ has one of the same meanings as $R_9$;

or a cosmetically or pharmaceutically acceptable acid addition salt thereof.

17. A compound according to claim 16, which is:

2-methyl-4-amino-6-ethoxypyrimidine 3-oxide;
2-methyl-4-amino-6-(2,4-dimethylphenyl)oxypyrimidine 3-oxide;
2-methyl-4-amino-6-(1-methyl)ethoxypyrimidine 3-oxide;
2-methyl-4-amino-6-butoxypyrimidine 3-oxide;
2-methyl-4-ethoxycarbonylamino-6-piperidinopyrimidine 3-oxide;
2,4-dimethyl-6-piperidinopyrimidine 3-oxide; or
the inner salt of 2,4-dimethyl-6-piperidino- 3-sulphoxypyrimidinium hydroxide.

* * * * *